(12) United States Patent
Pinaud et al.

(10) Patent No.: US 7,998,923 B2
(45) Date of Patent: Aug. 16, 2011

(54) BIOACTIVATION OF PARTICLES

(75) Inventors: Fabien Pinaud, Berkeley, CA (US);
David King, San Francisco, CA (US);
Shimon Weiss, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1460 days.

(21) Appl. No.: 10/513,567

(22) PCT Filed: May 7, 2003

(86) PCT No.: PCT/US03/14401
§ 371 (c)(1), (2), (4) Date: Nov. 3, 2004

(87) PCT Pub. No.: WO2004/039830
PCT Pub. Date: May 13, 2004

(65) Prior Publication Data
US 2008/0281079 A1  Nov. 13, 2008

Related U.S. Application Data

(60) Provisional application No. 60/378,720, filed on May 7, 2002.

(51) Int. Cl.
*A61K 38/00* (2006.01)
*A61K 51/00* (2006.01)
(52) U.S. Cl. .................... 514/1.1; 530/300; 424/1.69
(58) Field of Classification Search .................. None
See application file for complete search history.

(56) References Cited

U.S. PATENT DOCUMENTS

| | | | |
|---|---|---|---|
| 4,795,698 A | 1/1989 | Owen et al. | |
| 5,186,827 A | 2/1993 | Liberti et al. | |
| 5,200,084 A | 4/1993 | Liberti et al. | |
| 5,262,357 A | 11/1993 | Alivisatos et al. | |
| 5,466,574 A | 11/1995 | Liberti et al. | |
| 5,505,928 A | 4/1996 | Alivisatos et al. | |
| 5,512,332 A | 4/1996 | Liberti et al. | |
| 5,541,072 A | 7/1996 | Wang et al. | |
| 5,567,326 A | 10/1996 | Ekenberg et al. | |
| 5,698,271 A | 12/1997 | Liberti et al. | |
| 5,751,018 A | 5/1998 | Alivisatos et al. | |
| 5,795,470 A | 8/1998 | Wang et al. | |
| 5,866,099 A | 2/1999 | Owen et al. | |
| 5,990,479 A | 11/1999 | Weiss et al. | |
| 6,114,038 A | 9/2000 | Castro et al. | |
| 6,120,856 A | 9/2000 | Liberti et al. | |
| 6,194,213 B1 | 2/2001 | Barbera-Guillem | |
| 6,207,392 B1 | 3/2001 | Weiss et al. | |
| 6,221,602 B1 * | 4/2001 | Barbera-Guillem et al. | 435/6 |
| 6,261,779 B1 | 7/2001 | Barbera-Guillem et al. | |
| 6,274,323 B1 | 8/2001 | Bruchez et al. | |
| 6,306,610 B1 | 10/2001 | Bawendi et al. | |
| 6,319,607 B1 * | 11/2001 | Barbera-Guillem et al. | 428/402.24 |
| 6,326,144 B1 | 12/2001 | Bawendi et al. | |
| 6,333,110 B1 | 12/2001 | Barbera-Guillem | |
| 6,365,362 B1 | 4/2002 | Terstappen et al. | |
| 6,423,551 B1 | 7/2002 | Weiss et al. | |
| 6,444,143 B2 | 9/2002 | Bawendi et al. | |
| 6,468,808 B1 | 10/2002 | Nie et al. | |
| 6,544,732 B1 | 4/2003 | Chee et al. | |
| 6,620,627 B1 | 9/2003 | Liberti et al. | |
| 6,623,982 B1 | 9/2003 | Liberti et al. | |
| 6,630,307 B2 | 10/2003 | Bruchez et al. | |
| 6,645,731 B2 | 11/2003 | Terstappen et al. | |
| 6,649,138 B2 | 11/2003 | Adams et al. | |
| 6,767,702 B2 | 7/2004 | Mirkin et al. | |
| 6,777,186 B2 | 8/2004 | Mirkin et al. | |
| 6,815,064 B2 | 11/2004 | Treadway et al. | |
| 6,838,243 B2 | 1/2005 | Lai et al. | |
| 6,955,855 B2 | 10/2005 | Naasani | |
| 7,172,791 B2 | 2/2007 | Treadway et al. | |
| 7,198,847 B2 | 4/2007 | Naasani | |
| 7,205,048 B2 | 4/2007 | Naasani | |
| 7,214,428 B2 | 5/2007 | Naasani | |
| 7,368,086 B2 | 5/2008 | Naasani | |
| 2001/0034034 A1 | 10/2001 | Bruchez et al. | |
| 2002/0009728 A1 | 1/2002 | Bittner et al. | |

(Continued)

FOREIGN PATENT DOCUMENTS

EP  03 799 767.3-2107  8/2008

(Continued)

OTHER PUBLICATIONS

Peng, et al., Epitaxial Growth of Highly Luminescent CdSe/CdS; Core/Shell Nanocrystals with Photostability and Electronic Accessibility; Journal of the American Chemical Society, vol. 119, No. 30, 1997; pp. 7019-7029.
Akerman et al., "Nanocrystal Targeting In Vivo", Proc. Natl. Acad. Sci., v.99, n. 20 (Oct. 1, 2002) pp. 12617-12621.
PCT/US2005/009344 "Notification Concerning Transmittal of Int'l Prelim. Report on Patentability" and "Written Opinion of the ISA", mailed Oct. 5, 2006, U.S. Department of Health and Human Services.
Iyer et al. Solubilization of Quantum Dots with Recombinant Peptide and *Escherichia coli*. 2007. *Small*. 3(5): 793-798.
Kyte, J, Doolittle, R. A Simple Method for Displaying the Hydropathic Character of a Protein. 1982. *J Mol Biol*. 157: 105-132.

(Continued)

*Primary Examiner* — Maury Audet
(74) *Attorney, Agent, or Firm* — Venable LLP; Michael A. Gollin; Lars H. Genieser

(57) ABSTRACT

Particles are bioactivated by attaching bioactivation peptides to the particle surface. The bioactivation peptides are peptide-based compounds that impart one or more biologically important functions to the particles. Each bioactivation peptide includes a molecular or surface recognition part that binds with the surface of the particle and one or more functional parts. The surface recognition part includes an amino-end and a carboxy-end and is composed of one or more hydrophobic spacers and one or more binding clusters. The functional part(s) is attached to the surface recognition part at the amino-end and/or said carboxy-end.

43 Claims, 5 Drawing Sheets

U.S. PATENT DOCUMENTS

| | | |
|---|---|---|
| 2002/0028457 A1 | 3/2002 | Empedocles et al. |
| 2002/0127224 A1 | 9/2002 | Chen |
| 2002/0150905 A1 | 10/2002 | Barbera-Guillem et al. |
| 2003/0008414 A1 | 1/2003 | Nie et al. |
| 2003/0027214 A1 | 2/2003 | Kamb |
| 2003/0082237 A1 | 5/2003 | Cha et al. |
| 2003/0099940 A1 | 5/2003 | Empedocles et al. |
| 2003/0113709 A1 | 6/2003 | Alivisatos et al. |
| 2003/0129590 A1 | 7/2003 | Rosenthall et al. |
| 2003/0129591 A1 | 7/2003 | Rosenthall et al. |
| 2003/0148544 A1 | 8/2003 | Nie et al. |
| 2003/0165951 A1 | 9/2003 | Bruchez, Jr. et al. |
| 2003/0175773 A1 | 9/2003 | Chee et al. |
| 2004/0007169 A1 | 1/2004 | Ohtsu et al. |
| 2004/0009911 A1 | 1/2004 | Harris et al. |
| 2004/0014060 A1 | 1/2004 | Hoheisel et al. |
| 2004/0023415 A1 | 2/2004 | Sokolov et al. |
| 2004/0038307 A1 | 2/2004 | Lee et al. |
| 2004/0158051 A1 | 8/2004 | Ozkan et al. |
| 2004/0166505 A1 | 8/2004 | Bruchez et al. |
| 2004/0171039 A1 | 9/2004 | Bruchez et al. |
| 2004/0180380 A1 | 9/2004 | Lee et al. |
| 2005/0054004 A1 | 3/2005 | Alivisatos et al. |
| 2005/0059031 A1 | 3/2005 | Bruchez et al. |
| 2007/0172427 A1 | 7/2007 | Barchi et al. |
| 2008/0039816 A1 | 2/2008 | Svarovsky et al. |
| 2009/0253211 A1 | 10/2009 | Weiss et al. |

FOREIGN PATENT DOCUMENTS

| | | |
|---|---|---|
| GB | 2342651 | 4/2000 |
| JP | 2002-525394 | 8/2002 |
| WO | WO 00/17655 | 3/2000 |
| WO | WO 00/27365 | 5/2000 |
| WO | WO2004/039830 A2 | 5/2004 |
| WO | WO2004/039830 A3 | 2/2005 |
| WO | PCT/US2003/014401 | 3/2005 |
| WO | WO2005/053649 | 6/2005 |
| WO | WO 2005/053649 A1 | 6/2005 |
| WO | WO2005/093422 | 10/2005 |
| WO | WO 2005/093422 A2 | 10/2005 |
| WO | WO 2005/093422 A3 | 10/2005 |
| WO | WO 2006/093516 A2 | 9/2006 |

OTHER PUBLICATIONS

Hammes, BS, Carrano, CJ. Methylation of (2-Methylethanethiol-bis-3,5-dimethylpyrazolyl) methane Zinc Complexes and Coordination of the Resulting Thioether: Relevance to Zinc-Containing Alkyl Transfer Enzymes. 2001. *Inorg Chem.* 40:919-927.

Tobin et al. Structural Characterization of the Zinc Site in Protein Farnesyltransferase. 2003. *J Am Chem Soc.* 125(33):9962-9969.

Myers et al. Metal Coordination Sphere in the Methylated Ada Protein-DNA co-complex. 1994. *Chemistry & Biology.* 1(2): 91-97.

Huang et al. Evidence for a Catalytic Role of Zinc in Protein Farnesyltransferase. 1997. *Journal of Biological Chemistry.* 272(1):20-23.

International Search Report, date, issued in PCT/US2003/34897, mailed Aug. 20, 2004, U.S. Department of Health and Human Services.

International Search Report and Written Opinion of the International Searching Authority, issued in PCT/US2005/009344, mailed Dec. 21, 2005, U.S. Department of Health and Human Services.

International Preliminary Report on Patentability, issued in PCT/US2005/009344, mailed Oct. 5, 2006, U.S. Department of Health and Human Services.

International Preliminary Report on Patentability in PCT/US2005/022102, Dec. 28, 2006, The Regents of the University of California.

Written Opinion of the International Search Authority in PCT/US2005/022102, Nov. 7, 2006, The Regents of University of California.

International Search Report dated Nov. 7, 2006, issued in Nov. 7, 2006, issued in PCT/US2005/022102, mailed Nov. 7, 2006, The Regents of the University of California.

Vahrenkamp, H. Transitions, Transition States, Transition State Analogues: Zinc Pyrazolylborate Chemistry Related to Zinc Enzymes. 1999. *Acc Chem Res.* 32:589-596.

Pinaud et al. Bioactivation and Cell Targeting of Semiconductor CdSe/ZnS Nanocrystals with Phytochelatin-Related Peptides. 2004. *J Am Chem Soc.* 126, 6115-6123.

Wu et al. Immunofluorescent Labeling of Cancer Marker Her2 and other Cellular Targets with Semiconductor Quantum Dots. 2003. *Nature Biotechnology.* 21:41-46.

Kyte, J. et al., "A Simple Method for Displaying the Hydropathic Character of a Protein", J. Mol. Biol. 157 (1982) 105-132.

Pinaud et al., "Supporting information for Bioactivation and Cell Targeting of Semiconductor CdSe/ZnS Nanocrystals with Phytochelatin-related Peptides", S-1- S-11, published online (Web) at http://pubs.acs.org/doi/suppl_10.1021/ja031691c (file http://pubs.acs.org/doi/suppl/10.1021/ja031691c/suppl_file/ja031691csi20040223_054743.pdf) on Apr. 22, 2004, together with Pinaud et al., "Bioactivation and Cell Targeting of Semiconductor CdSe/ZnS Nanocyrstals with Phytochelatin-Related Peptides", J. Am. Chem. Soc., 126(19) (2004) 6115-6123.

Pinaud et al., "Supporting information for Bioactivation and Cell Targeting of Semiconductor CdSe/ZnS Nanocrystals with Phytochelatin-related Peptides", S-1- S-11, published online (Web) at http://pubs.acs.org/doi/suppl/10.1021/ja031691c (file http://pubs.acs.org/doi/suppl/10.1021/ja031691c/suppl_file/ja031691csi20040223_054948.pdf) on Apr. 22, 2004, together with Pinaud et al., "Bioactivation and Cell Targeting of Semiconductor CdSe/ZnS Nanocyrstals with Phytochelatin-Related Peptides", J. Am. Chem. Soc., 126(19) (2004) 6115-6123.

Michalet et al. Properties of Fluorescent Semiconductor Nanocrystals and their Application to Biological Labeling (2001) Single Molecules 2, 261-276.

Alivisatos, P. The use of nanocrystals in biological detection. (2004) Nature Biotechnology 22, 47-52.

Hines, M. A., Guyot-Sionnest, P. Synthesis and Characterization of Strongly Luminescing ZnS-Capped CdSe Nanocrystals. (1996) Journal of Physical Chemistry. 100, 468-471.

Dabbousl et al. (CdSe) ZnS Core-Shell Quantum Dots: Synthesis and Characterization of a Size Series of Highly Luminescent Nanocrystallites. (1997) Journal of Physical Chemistry B 101, 9463-9475.

Tsay et al. Hybrid Approach to the Synthesis of Highly Luminescent CdTe/ZnS and CdHgTe/ZnS Nanocrystals (2004) Journal of the American Chemical Society 126, 1926-1927.

Bruchez et al. Semiconductor Nanocrystals as Fluorescent Biological Labels. (1998) Science 281, 2013-2016.

Gerion et al. Synthesis and Properties of Biocompatible Water-Soluble Silica-Coated CdSe/ZnS Semiconductor Quantum Dots. (2001) Journal of Physical Chemistry B 105, 8861-8871.

Chan, W. C. W., Nie, S. M. Quantum Dot Bioconjugates for Ultrasensitive Nonisotopic Detection. (1998) Science 281, 2016-2018.

Guo et al. Luminescent CdSe/CdS Core/Shell Nanocrystals in Dendron Boxes: Superior Chemical, Photochemical and Thermal Stability. (2003) J Am Chem Soc 125, 3901-9.

Larson et al. Water-Soluble Quantum Dots for Multiphoton Fluorescence Imaging in Vivo. (2003) Science 300, 1434-6.

Dubertret et al. In Vivo Imaging of Quantum Dots Encapsulated in Phospholipid Micelles. (2002) Science 298, 1759-62.

Mattoussi et al. Bioconjugation of Highly Luminescent Colloidal CdSe—ZnS Quantum Dots with an Engineered Two-Domain Recombinant Protein. (2001) Physica Status Solidi B-Basic Research 224, 277-283.

Kim, S., Bawendi, M. G. Oligomeric Ligands for Luminescent and Stable Nanocrystal Quantum Dots. (2003) J Am Chem Soc 125, 14652-3.

Pinaud et al. Bioactivation and Cell Targeting of Semiconductor CdSe/ZnS Nanocrystals with Phytochelatin-Related Peptides. (2004) J. Am. Chem. Soc. 126, 6115-6123.

Manna et al. Epitaxial Growth and Photochemical Annealing of Graded CdS/ZnS Shells on Colloidal CdSe Nanorods (2002) Journal of the American Chemical Society. 124, 7136-7145.

Murray et al. Synthesis and Characterization of Nearly Monodisperse CdE (E = S, Se, Te) Semiconductor Nanocrystallites. (1993) Journal of the American Chemical Society 115, 8706-8715.

Peng, Z. A., Peng, X. G. Nearly Monodisperse and Shape-Controlled CdSe Nanocrystals via Alternative Routes: Nucleation and Growth. (2002) Journal of the American Chemical Society 124, 3343-3353.

Li et al. Large-Scale Synthesis of Nearly Monodisperse CdSe/CdS Core/Shell Nanocrystals Using Air-Stable Reagents via Successive Ion Layer Adsorption and Reaction (2003) Journal of the American Chemical Society 125, 12567-12575.

Talapin et al. Highly Luminescent Monodisperse CdSe and CdSe/ZnS Nanocrystals Synthesized in a HexadecylamineTrioctylphosphineOxideTrioctylphospine Mixture. (2001) Nano Letters 1, 207-211.

Magde et al. Fluorescence Correlation Spectroscopy. 11. An Experimental Realization. (1974) Biopoymers 13, 29-61.

Rigler et al. (1993) European Biophysics Journal 22, 169-175.

Ebenstein et al. Fluorescence quantum yield of CdSe/ZnS nanocrystals investigated by correlated atomic-force and single-particle fluorescence microscopy. (2002) Applied Physics Letters 80, 4033- 4035.

www.qdots.com/new/technology, Quantum Dot Corporation, Oct. 21, 2003 (15 pages).

Barchi, JJ., Svarosky, S., "Glycononotechnology: Construction and Properties of Sugar/Peptide-Bearing Nanoparticles", slide presentation Boston, MA, May 5, 2003 (19 pages).

Chan et al., "Luminescent Quantum Dots for Multiplexed Biological Detection and Imaging", *Current Opinion in Biotechnology* 2002, vol. 13, Elsevier Science, Ltd. (pp. 40-46).

Wang et al., "Stabilization of Inorganic Nanocrystals by Organic Dendrons", *J. Am. Chem. Soc.* vol. 124, No. 10, Feb. 14, 2002 (pp. 2293-2298).

Liang et al., "Functionalized CdSe quantum dots as selective silver ion chemodosimeter", Analyst, 129(7), Jul. 2004, pp. 619-622.

(Search 3) Results of LEXIS search performed Sep. 2004. Search string = (quantum dot or quantum confin! or nanocrystal!) and bio! and (mercapto! or thio!).

Chen, "Synthesis of Glyconanospheres Containing Luminescent CdSe-ZnS Quantum Dots", *Nano Letters*, vol. 3, No. 5, 2003 (pp. 581-584).

Communication of Aug. 25, 2008 in European Patent Application No. EP 03 799 767.3-2107.

X.Michalet et al., "Quantum dots for live cells, in vivo imaging, and diagnostics", Science, 307 (2005) 538-544.

X.Michalet et al., "The power and prospects of fluorescence microscopies and spectroscopies", Annu. Rev. Biophys. Biomol. Struct., 32 (2003) 161-182.

F.Pinaud et al., "Advances in fluorescence imaging with quantum dot bio-probes", Biomaterials, 27 (2006) 1679-1687.

Interview Summary dated Jul. 7, 2009 for U.S. Appl. No. 11/630,584.

U.S. Patent and Trademark Office Action dated Apr. 2, 2009 for U.S. Appl. No. 11/630,584.

* cited by examiner

FIG. 5

SEQUENCE LISTING

```
<160> NUMBER OF SEQ ID NOS: 11

<210> SEQ ID NO 1
<211> LENGTH: 10
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 1, 4, 7 and 10
<223> OTHER INFORMATION: Xaa is ala substituted with a hydrophobic
      group

<400> SEQUENCE: 1

Xaa Cys Cys Xaa Cys Cys Xaa Cys Cys Xaa
 1               5                  10

<210> SEQ ID NO 2
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11, 14, 17 and 20
<223> OTHER INFORMATION: Xaa is ala substituted with a hydrophobic
      group

<400> SEQUENCE: 2

Gly Ser Glu Ser Gly Gly Ser Glu Ser Gly Xaa Cys Cys Xaa Cys Cys
 1               5                  10                  15

Xaa Cys Cys Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11, 14, 17 and 20
<223> OTHER INFORMATION: Xaa is ala substituted with a hydrophobic
      group

<400> SEQUENCE: 3

Gly Ser Ser Ser Gly Gly Ser Ser Ser Gly Xaa Cys Cys Xaa Cys Cys
 1               5                  10                  15

Xaa Cys Cys Xaa
            20
```

```
<210> SEQ ID NO 4
<211> LENGTH: 29
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 20, 23, 26 and 29
<223> OTHER INFORMATION: Xaa is ala substituted with a hydrophobic
      group

<400> SEQUENCE: 4

Gly Pro Lys Lys Lys Arg Lys Val Gly Gly Ser Glu Ser Gly Gly Ser
 1               5                  10                  15

Glu Ser Gly Xaa Cys Cys Xaa Cys Cys Xaa Cys Cys Xaa
                20                  25

<210> SEQ ID NO 5
<211> LENGTH: 21
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 12, 15, 18 and 21
<223> OTHER INFORMATION: Xaa is ala substituted with a hydrophobic
      group

<400> SEQUENCE: 5

Lys Gly Ser Glu Ser Gly Gly Ser Glu Ser Gly Xaa Cys Cys Xaa Cys
 1               5                  10                  15

Cys Xaa Cys Cys Xaa
                20

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Gly Ser Glu Ser Gly Gly Ser Glu Ser Gly
 1               5                  10

<210> SEQ ID NO 7
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 7

Gly Ser Ser Ser Gly Gly Ser Ser Ser Gly
 1               5                  10

<210> SEQ ID NO 8
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 8

Gly Pro Lys Lys Lys Arg Lys Val Gly Gly Ser Glu Ser Gly Gly Ser
 1               5                  10                  15
```

Glu Ser Gly

<210> SEQ ID NO 9
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 9

Lys Gly Ser Glu Ser Gly Gly Ser Glu Ser Gly
 1               5                  10

<210> SEQ ID NO 10
<211> LENGTH: 20
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: 11, 14, 17, 20
<223> OTHER INFORMATION: Xaa is ala substituted with a hydrophobic
      group

<400> SEQUENCE: 10

Gly Ser Glu Ser Gly Gly Ser Glu Ser Gly Xaa Cys Cys Xaa Cys Cys
 1               5                  10                  15

Xaa Cys Cys Xaa
             20

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Xaa is Ala substituted with a hydrophobic
      group
<220> FEATURE:
<221> NAME/KEY: MOD_RES
<222> LOCATION: (4)..(4)
<223> OTHER INFORMATION: Xaa is Ala substituted with a hydrophobic
      group
<220> FEATURE:
<221> NAME/KEY: MOD_RES
<222> LOCATION: (7)..(7)
<223> OTHER INFORMATION: Xaa is Ala substituted with a hydrophobic
      group
<220> FEATURE:
<221> NAME/KEY: MOD_RES
<222> LOCATION: (10)..(10)
<223> OTHER INFORMATION: Xaa is Ala substituted with a hydrophobic
      group
<220> FEATURE:
<221> NAME/KEY: misc_feature
<222> LOCATION: (2)..(10)
<223> OTHER INFORMATION: This region may encompass 1 to 3 'Cys Cys Xaa'
      repeating units

<400> SEQUENCE: 11

Xaa Cys Cys Xaa Cys Cys Xaa Cys Cys Xaa
 1               5                  10

BIOACTIVATION OF PARTICLES

This application is a National Stage of International Application No. PCT/US2003/014401, filed May 7, 2003, which claims the benefit of U.S. Provisional Application No. 60/378,720, filed May 7, 2002. International Application No. PCT/US2003/014401 is hereby incorporated by reference in its entirety, and U.S. Provisional Application No. 60/378,720 is hereby incorporated by reference in its entirety.

This invention was made with Government support of Grant Nos. EB000312 and RR014891 awarded by the National Institutes of Health and Grant No. DE-AC03-76SF00098 awarded by the Department of Energy. The Government has certain rights in this invention.

BACKGROUND OF THE INVENTION

1. Field of the Invention

The present invention relates generally to microparticles and/or nanoparticles that may be used in biological systems. More particularly, the present invention is directed to modifying the surface chemistry of such particles, without using conventional linking agents, to enhance their compatibility with biological systems and to also provide the particles with one or more biological functions.

2. Description of Related Art

Fluorescent labeling of biological systems is a well-known analytical tool used in modern biotechnology as well as analytical chemistry. Applications for such fluorescent labeling include technologies such as medical (and non-medical) fluorescence microscopy, histology, flow cytometry, fluorescence in-situ hybridization (medical assays and research), DNA sequencing, immunoassays, binding assays, separation, etc.

Conventionally, such fluorescent labeling involves the use of an organic dye molecule bonded to a moiety that, in turn, selectively bonds to a particular biological system, the presence of which is then identified by excitation of the dye molecule to cause it to fluoresce. There are a number of problems with such an analytical system. In the first place, the emission of light of visible wavelengths from an excited dye molecule usually is characterized by the presence of a broad spectrum, i.e., the entire emission spectrum is rather broad. As a result, there is a severe limitation on the number of different color organic dye molecules which may be utilized simultaneously or sequentially in an analysis since it is difficult to either simultaneously or even non-simultaneously detect or discriminate between the presence of a number of different detectable substances due to the broad spectrum emissions and emission tails of the labeling molecules. Another problem is that most dye molecules have a relatively narrow absorption spectrum, thus requiring either multiple excitation beams used either in tandem or sequentially for multiple wavelength probes, or else a broad spectrum excitation source which is sequentially used with different filters for sequential excitation of a series of probes respectively excited at different wavelengths.

Another problem frequently encountered with existing dye molecule labels is that of photostability. Available fluorescent molecules bleach, or irreversibly cease to emit light, under repeated excitation ($10^4$-$10^8$ cycles of absorption/emission). These problems are often surmounted by minimizing the amount of time that the sample is exposed to light, and by removing oxygen and/or other radical species from the sample. In addition, the probe tools used for the study of systems by electron microscopy techniques are completely different from the probes used for study by fluorescence. Thus, it is not possible to label a material with a single type of probe for both electron microscopy and for fluorescence. This is also the case for multifunctional molecular imaging: Fluorescence+MRI; Fluorescence+PET; Fluorescence+CT; Fluorescence+MRI+PET+CT and any other combination, not even including fluorescence, such as MRI+PET, CT+EM. It would, therefore, be desirable to provide a stable probe material for biological and biomedical applications preferably having a wide absorption band and capable of providing a detectable signal in response to exposure to energy, without the presence of the large red emission tails characteristic of dye molecules (thereby permitting the simultaneous use of a number of such probe materials, each, for example, emitting light of a different narrow wavelength band) and/or capable of scattering or diffracting radiation. It would also be equally desirable to provide a single, stable probe material that can be used to image the same sample by both light and electron microscopy, such as MRI/PET/CT with or without fluorescence.

Semiconductor nanocrystals (NCs or quantum dots) are fragments of semiconductor material composed of a few hundreds to thousands of atoms. Quantum dots have very interesting optical properties resulting from quantum confinement. This confinement occurs when the particles are smaller than the Bohr exciton radius of the material they are composed of.

Since the first synthesis of semiconductor nanoparticles, significant progress has been made to control the size and monodispersion of quantum dots in a range of 1 to 7 nanometers (nm). A special interest was given to quantum dots made from material from the II-IV class such as cadmium and selenide (CdSe). CdSe particles covered with a second layer of zinc/sulfide (CdSe/ZnS) emit a strong fluorescent signal in the visible part of the light spectra. Varying the size of the nanocrystals made of these materials by few nanometers allows the tuning of the emission wavelength while the absorption characteristics are similar for each size.

The chemical synthesis of CdSe/ZnS quantum dots requires a hydrophobic environment and surfactant such as trioctylphosphine oxide (TOPO) in order to control the nucleation between Cd and Se and the growth of the particles. This results in highly hydrophobic particles, poorly soluble in aqueous environments. For biological application using quantum dots as probes, a surface chemistry is thus necessary to remove the surfactant and make the particle biocompatible and soluble in aqueous solvents.

U.S. Pat. Nos. 6,207,392 and 6,423,551 disclose semiconductor nanocrystal probes for biological applications and processes for making and using such probes. The probes include semiconductor nanocrystals, linking agents and affinity molecules. The contents of this patent are hereby incorporated by reference in its entirety.

In U.S. Pat. No. 5,990,479 organo luminescent semiconductor nanocrystal probes for biological applications and process for making and using such probes are disclosed. The contents of this patent are hereby incorporated by reference in its entirety.

SUMMARY OF THE INVENTION

In accordance with the present invention, particles are bioactivated by attaching bioactivation peptides to the particle surface. The bioactivation peptides are peptide-based compounds that impart one or more biologically important functions to the particles. Each bioactivation peptide includes a molecular or surface recognition part that binds with the surface of the particle and one or more functional parts. The surface recognition part includes an amino-end and a carboxy-end and is composed of one or more hydrophobic spacers and one or more binding clusters. The functional part(s) is attached to the surface recognition part at the amino-end and/or said carboxy-end.

The present invention provides a method for modulating surface chemistry properties of particles using bioactivation peptides as an organic interface between the particle surface and aqueous media. The peptides provide water solubility and bioactivity to inorganic/metallic/semiconducting nanoparticles as well as organic particles. The use of other prior art compounds (linkers, linking agents) to provide activity and/or solubility to the particle is not necessary. A single bioactivation peptide in accordance with the present invention has a molecular or surface recognition part (MRP or SRP) for the nanoparticle and a functional part (FP). The functional part is attached to one or both ends of the SRP and can include a wide variety of functional agents including a molecular recognition agent for targeting or a chemical handle (conjugation agent) for bioconjugation. The SRP of the bioactivation peptide SRP provides adequate (amino acids) characteristics for the interface between the particle surface and an organic surface (functional agent), and gives the particles protein-like properties. The bioactivation peptide can provide targeting capabilities to the particles by way of interchangeable (signal) sequences and/or addition (conjugation) of a nucleic acid/peptide/protein/antibody already bearing a moiety capable of biorecognition and binding.

The above discussed and many other features and attendant advantages of the present invention will become better understood by reference to the detailed description when taken in conjunction with the accompanying drawings.

BRIEF DESCRIPTION OF THE DRAWINGS

FIG. 5 is a pictorial representation of the treatment of a particle with a mixture of two bioactivation peptides.

DETAILED DESCRIPTION OF THE INVENTION

Figure 1:
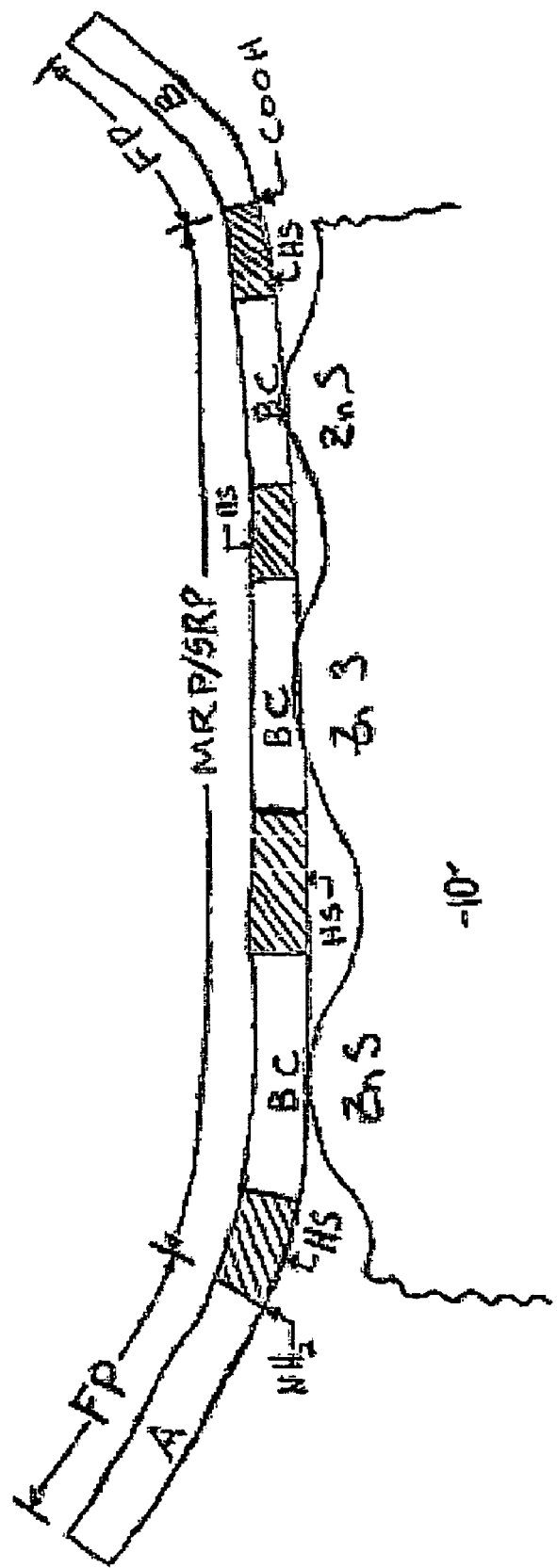
FIG. 1 is a diagrammatic representation of a bioactivation peptide in accordance with the present invention attached to the surface of a particle.

The present invention generally involves converting particles that are biologically non-functional into bioactivated particles that have one or more functional characteristics that are necessary to make the particles useful in biological systems. This is accomplished by attaching bioactivation peptides to the surface of the particles. These specialized peptides are capable of imparting one or more biologically important functions to the particles. As will be discussed in detail below, the bioactivation peptides of the present invention effectively eliminate the need for conventional lining agents that have been used in the past to connect biologically functional groups to particle surfaces. In addition, the use of bioactivation peptides to impart biological function(s) to particles is extremely versatile and relatively simple. It has wide applications to any type of biological system where particles having specific biological functions are required.

The term "bioactivated particle" is intended to mean any particle that has been treated with bioactivation peptides of the present invention so that the particle has one or more biological functions that it otherwise would not have. Examples of the types of functions that can be imparted to particles using the bioactivation peptides of the present invention include solubility in aqueous mediums, bioconjugation, targeting, therapy, imaging, detection, recognition and diagnosis.

Numerous types of particles having a wide range of sizes and compositions may be bioactivated. The particles should be sufficiently small to be able to form colloids in solution. The bioactivation peptides may be used to impart biological functions to any of the particles that are used in biological systems and which typically require the use of a linking agent or other surface treatment in order to attach biologically active materials to the particle. Nanoparticles are preferred particles for bioactivation. Such particles will have particle sizes ranging from 0.1 to 100 nanometers. Microparticles having diameters up to about 100 microns may also be bioactivated. Quantum dots as described in the previously referenced patents are particularly well suited for bioactivation using bioactivation peptides in accordance with the present invention. The present invention applies to all types of particle shapes, such as nanowires, nanotubes and nanorods. The bioactivation peptides can bind to the surface of arbitrarily shaped particles, not just spherical micro or nanoparticles.

The invention may be used to treat particles having a wide range of compositions. Particles composed of inorganic and/or organic materials may be used. Inorganic particles are preferred particles for bioactivation. As mentioned above, the invention may be used to bioactivate any of the various types of particles that typically require initial treatment with linking agents in order to be used in biological systems. Examples of specific particles, such as nanocrystals and semiconductor nanocrystals, are set forth below in more detail.

A bioactivation peptide in accordance with the present invention is shown diagrammatically in FIG. 1. The bioactivation peptide includes a molecular recognition part (MRP), which is also referred to herein as the surface recognition part (SRP). The SRP is shown bound to the surface of a quantum dot that is composed of a ZnS coated CdSe core. The ZnS coating is shown at 10 and is used only for demonstrative purposes. The bioactivation peptide further includes a functional part that is located at one or both ends of the SRP as shown at "A" and "B". The functional part is made up of one or more functional agents that impart one or more biological functions to the particle.

The SRP is made up of binding clusters (BC's) and hydrophobic spacers (HS's). As few as one binding cluster and one hydrophobic spacer may be used to form the SRP. However, it is preferred that at least two or more BC's and HS's be used. As shown in FIG. 1, the SRP/MRP includes three BC's and four HS's that alternate sequentially along the SRP. As is the case in any amino acid sequence, the SRP has an amino end and a carboxy end (See FIG. 1). Although it is preferred that a HS be located between each BC, it is not necessary. SRP's are possible where BC's and HS's are grouped together. The number of BC's and HS's that are needed to bind the bioreactive peptide to a given particle surface will vary depending upon a number of parameters including the number of functional agents present in the functional part and the chemical characteristics of the functional agents. In addition, the type of particle surface as well as the particular amino acids used in the SRP must be taken into consideration. The particular number and types of BC's and HS's, as well as their orientation, can be determined by routine experimentation for each different type of particle and functional part.

The BC's are made up of one or more natural or unnatural amino acids or amino acid derivatives that are capable of binding to the particle surface. Exemplary amino acids include cysteine, methionine, histidine and derivatives thereof. The derivatives may be natural or unnatural. Exemplary amino acid derivatives include 3,3-diphenyl-Ala—OH, 2-amino-3,3-dimethylbutyric acid, (Also see http://www.sigmaaldrich.com/img/assets/6040/chemFiles_v1n5_unnaturalaa_small.pdf). The BC preferably includes two amino acids or derivatives and may include as many as 10 amino acids or derivatives. The particular amino acids or derivatives that are used to form the SRP may be the same or different. The make-up of the BC's for any given SRP will vary depending upon the particular functional parts being used and the intended particular particle surface for attachment. The BC make-up can be determined by routine experimentation once the particle to be bioactivated has been selected and the functional agent(s) has been chosen.

The HS's are composed of a compound that is hydrophobic and capable of binding with the BC's. Although any number of hydrophobic compounds can be used, it is preferred that the HS's include one or more natural or unnatural amino acids or derivatives that have been modified to be hydrophobic. Exemplary modified amino acids include hydrophobic alanine, hydrophobic glycine, hydrophobic isoleucine, hydrophobic leucine, hydrophobic methionine, hydrophobic arginine, hydrophobic valine, hydrophobic tryptophan and derivatives thereof. The preferred modification is to substitute a cyclohexyl group into the amino acid in place of H from the methyl group. Other hydrophobic groups, such as benzene, may be used in place of cyclohexyl. It is preferred that the HS contain a single hydrophobic amino acid. However, up to 10 hydrophobic amino acids may be present in any one HS.

Figure 2:
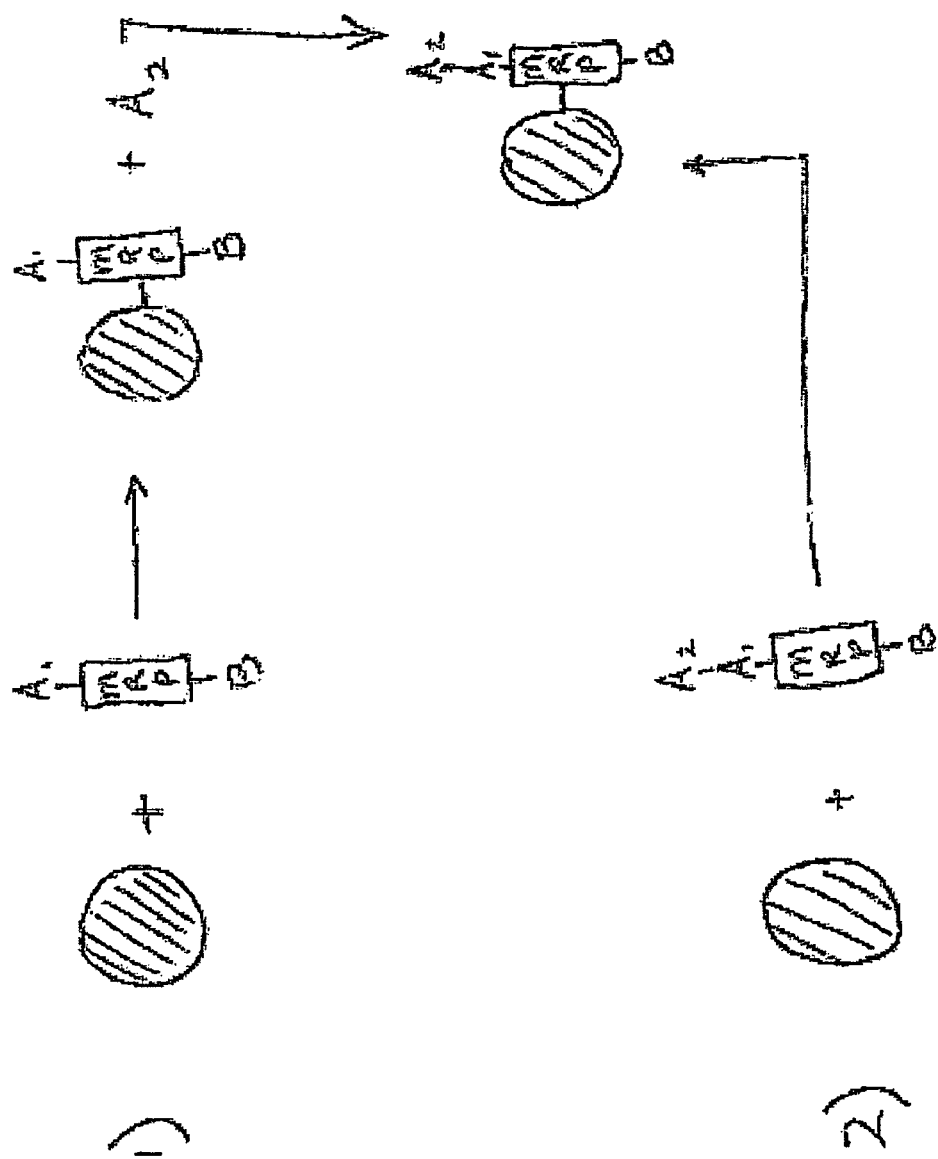
FIG. 2 is a diagrammatic representation of alternate method for making bioactivation particles in accordance with the present invention.

The functional part (FP) of the bioactivation peptide includes functional agents attached to either the amino end of the SRP (A), the carboxy end of the SRP (B) or both. The functional agent may be anything that is intended to impart a biological function to the particle. Exemplary functional agents include solubility agents, conjugation agents, targeting agents, therapeutic agents, imaging agents, detection agents, recognition agents and diagnostic agents. There may be some overlap in agents since some compounds may serve a dual purpose. The functional agent must be able to bind to the SRP or one of the other agents. The functional part may contain as few as one functional agent, such as a solubility agent, attached to only one end of the SRP. At the other extreme, two, three or more functional agents can be attached to one or both ends of the SRP.

For bioactivation peptides that are used to treat particles that are not soluble in aqueous media, it is preferred that a solubility agent be included in the functional part as a minimum. Although the solubility agent may be located anywhere, it is preferred that it is attached directly to one or both ends of the SRP. An exemplary solubility agent is a hydrophilic peptide that has from 1 to 100 amino acids. Specific examples include gly-ser-glu-ser-gly-gly-ser-glu-ser-gly (SEQ. ID. NO. 6), gly-ser-ser-ser-gly-gly-ser-ser-ser-gly (SEQ. ID. NO. 7). Numerous other hydrophilic peptides are possible. The solubility agent may also be other known hydrophilic compounds that can be attached to the SRP or a bioconjugation agent. Exemplary other solubility agents include polyethylene glycol, poly(ethylene oxide), polyelectrolytes and sugars. Sugars, such as cellobiose, sucrose and sialic acid are suitable. Exemplary polyelectrolytes include polyethylene immine.

The following is a list of various functional agents, other than solubility agents, that is intended to be exemplary only. As will be appreciated numerous other functional agents may be attached to the SRP to form bioactivation peptides in accordance with the present invention.

Conjugation agents: biotin, avidin, streptavidin and derivatives, lysine, cysteine, aspartic acid, glutamic acid-terminated peptides (with reactive groups amines, thyoles, carboxyl, unnaturals, keto).

Targeting agents: antibodies, enzyme substrate, receptor ligands.

Therapeutic agents: taxol, herceptin.

Imaging agents: Fluorescin, bromophenyl blue, Iodine, Yttrium, Tritium, Metallotexaphyrins, many radioactive reagents, MRI enhancing reagents, PET, CT, etc.

Detection agents: the same or similar to the above-listed imaging agents.

Recognition agents: same imaging/therapeutics conjugated to antibodies and/or recognition peptides.

Diagnostic agents: any of the above listed agents may be used as a diagnostic agent.

Demonstrative examples of bioactivation peptides in accordance with the present invention are listed below Bioactivation Peptides with Solubility/Conjugation Agents (amide or acetyl)-MRP-hydrophilic peptide-biotin or avidin/istreptavidin biotin-hydrophilic peptide-MRP-carboxamide biotin-MRP-carboxamide carboxamide-MRP-hydrophilic peptide-NHS ester carboxamide-MRP-hydrophilic peptide-keto group DNA oligo-hydrophilic peptide-MRP-carboxamide keto, thiols will allow orthogonal conjugation to different peptides (on the same nanoparticles or on different particles in the same suspension)

Bioactivation Peptides with Solubilty/Tumor Targeting Agents:

(amide or acetyl)-MRP-hydophilic peptide-transferrin (or an antibody to one of the tumor receptors transferrin-hydrophilic peptide-MRP-carboxamide tumor targeting sequence-hydrophilic peptide MRP-carboxamide DNA oligo-hydrophilic peptide-MRP-carboxamide transferrin-hydrophilic peptide-MRP-hydrophillic peptide-tranferrin Other agents include antibody, minibody, single chain fragment, . . .

Bioactivation Peptides with Solubility Agents

Amide or acetyl-MRP-hydrophilic peptide hydrophilic peptide-MRP-carboxyl hydrophilic peptide-MRP-carboxamide succinyl-hydrophilic peptide-MRP-carboxamide hydophilic peptide-MRP-hydrophilic peptide PEG-hydrophilic peptide-MRP-carboxamide PEG-MRP-hydrophilic peptide Other exemplary functional agents include 1,4,7,10-tetraazacyclodoecane-1,4,7,10-tetraacetic acid (DOTA), Ni-NTA, I, Yt, C as well as many types of chelators, metallic ions, isotopes, and magnetic materials.

The MRP of the bioactivation peptides may be made by simple peptide synthesis protocols that are well established. The various functional agents are attached to the MRP or other functional agent by peptide synthesis or known conjugation techniques for the particular agent. The bioactivation peptides may be completely synthesized with all of its functional agents being attached prior to mixing with particles. Alternately, a bioactivation peptide may be attached to a particle with only part of the total intended functional agents attached. The remainder of the functional agents may then be attached at a later time. Referring to FIG. 2, the two above procedures are diagrammatically shown for making the same bioactivated particle in which the bioactivation peptide is $A_1$-$A_2$–MRP–B. In the top portion of FIG. 2, a bioactivation peptide, ($A_1$-MRP-B) is mixed with the particles to form a bioactivated particle having $A_1$ and B functionality. This bioactive particle is then mixed with $A_2$ to form the final bioactivated particles that has $A_1$, $A_2$ and B functionality. This type of two-step procedure is particularly useful when $A_1$ is a solubility agent that is used to form a "stock" solution of soluble particles that can be used immediately or stored for use at a later time to form bioactivated particles having a number of different $A_2$ functional agents. As shown at the bottom of FIG. 2, the $A_1$-$A_2$-MRP–B bioactivated particle can also be made in a single step.

The preceding single and multiple step synthesis protocols are exemplary only with it being understood that the same basic procedures may be used to produce bioactivated particles having many more functional agents attached to one or both ends the MRP. In addition, FIG. 2 only shows the addition of a single type of bioactivation peptide to the particle. In many situations, it is desirable to attach different bioactivation peptides to the same particle. Each of the bioactivation peptides may carry a single different functional agent or they may each have multiple functional agents.

An example of a bioactivated particle having multiple bioactivation peptides is set forth below. The bioactivated particle provides for targeting, imaging and therapy all in one vehicle. The bioactivated particle is formed by simply treating the particle with the following mixture of four different bioactivation peptides:

| | |
|---|---|
| 1) MRP-peg + | solubility agent |
| 2) MRP-hydrophilic peptide-transferrin + | targeting agent |
| 3) MRP-hydrophilic peptide-tyrosin-DOTA-Iodine + | (nuclear) imaging agent |
| 4) MRP-hydrophilic peptide-therapeutic molecue | therapeutic agent |

Another example involves treating the particle to be bioactivated with a multi-functional bioactivation peptide as follows

| | |
|---|---|
| 1) MRP-peg-biotin | solubility agent + targeting agents |
| 2) MRP-peg-NLS-biotin | solubility agent + targeting/detection agent 1 + targeting/detection agent 2 |
| 3) MRP-hydrophilic peptide -targeting sequence- protease cleavage sequence- membrane crossing sequence | solubility agent + targeting/detection agent 1 + substrate + recognition/targeting agent 2 |

The following examples demonstrate some of the many different types of bioactivation peptides and bioactivated particles that can be prepared and used in accordance with the present invention. The bioactivation peptides set forth in these example have the formula:

A-[Ala-C-C-Ala-C-C-Ala-C-C-Ala]-B where the central sequence is the SRP (MRP) and A and B are the functional parts. A and B are either the same or different and independently comprise a polypeptide group, an acetyl group, an amine group, a carboxamide group or a biotin group, Ala is alanine substituted with a hydrophobic group, and C is cysteine.

Preferred hydrophobic groups are cyclohexyl groups, thus a preferred bioactivation peptide coating for particles, such as semiconductor nanocrystals, have the sequence Cha-C-C-Cha-C-C-Cha-C-C-Cha (SEQ. ID. NO. 1), where Cha is cyclohexyl alanine.

The bioactivation peptides are applied directly to semiconductor nanocrystals without the use of a separate linking agent. The bioactivation peptide gives the particles molecular recognition capabilities and water/buffer solubility. The particles can be conjugated to other molecules and can be given other desired properties by the large diversity offered by amino acids (hydrophobic/hydrophilic interactions and ionic/charge interactions). The invention is useful for NCs fluorescent probe targeting, targeting of particles to body parts (tumors) for x-ray medical imaging (x-ray of element specific core level and possibly others) and for x-ray photodynamic/photothermal therapy (delivering free radicals/heat to element specific core level via absorption of monochromatic x-ray).

The bioactivation peptides also allow self-assembly of organic-inorganic nanostructure hybrids by molecular recognition. They allow interfacing enzymes, biocatalysts and other proteins/RNA catalysts to nanoparticles to produce nano-machines/molecular machines that can be activated by light and/or charge. For examples charge generated by light in the nanoparticle can be separated and transferred to the protein to trigger enzymatic reaction, catalysis etc. (yielding, for example, light activated/triggered therapeutics.

By use of the terms "nanometer crystal" or "nanocrystal" herein is meant an organic or inorganic crystal particle, preferably a single crystal particle, having an average cross-section no larger than about 20 nanometers (nm) or $20 \times 10^{-9}$ meters (200 Angstroms), preferably no larger than about 10 nm (100 Angstroms) and a minimum average cross-section of about 1 nm, although in some instances a smaller average cross-section nanocrystal, i.e., down to about 0.5 nm (5 Angstroms), may be acceptable. Typically the nanocrystal will have an average cross-section ranging in size from about 1 nm (10 Angstroms) to about 10 nm (100 Angstroms).)

By use of the term "semiconductor nanocrystal" is meant a nanometer crystal or nanocrystal of Group II-VI and/or Group III-v semiconductor compounds capable of emitting electromagnetic radiation upon excitation, although the use of Group IV semiconductors such as germanium or silicon, or the use of organic semiconductors, may be feasible under certain conditions.

The term "radiation," as used herein, is meant to include electromagnetic radiation, including x-ray, gamma, ultra-violet, visible, infrared, and microwave radiation; and particle radiation, including electron beam, beta, and alpha particle radiation.

The term "energy" is intended to include electromagnetic radiation, particle radiation, and fluorescence resonance energy transfer (FRET). As used herein, the term "first energy is meant the energy to which a semiconductor nanocrystal, within a semiconductor nanocrystal compound or within a semiconductor nanocrystal probe, in response to exposure to a first energy. It should be noted that different nanocrystals, when exposed to the same "first energy," may respectively pronide "second energies" which differ from one another, and the use of the term "second energy," when used in connection with a plurality of semiconductor nanocrystals will be understood to refer to either second energies which are the same or to a plurality of different second energies.

By the use of the term "energy transfer" is meant the transfer of energy from one atom or molecule to another atom or molecule by either radiative or non-radiative pathways.

The term "proximal source" is meant an atom, a molecule, or any other substance that is capable of transferring energy to and/or receiving energy transferred from another atom or molecule or any other substance.

The term "proximal structure" as used herein may be an atom, a molecule, or any other substance (e.g., a polymer, a gel, a lipid bilayer, and any substance bonded directly to a semiconductor nanocrystal probe) that is capable of receiving energy transferred from another atom or molecule or other substance (including a semiconductor nanocrystal probe).

By use of the term "a narrow wavelength band," with regard to the electromagnetic radiation emission of the semiconductor nanocrystal, is meant a wavelength band of emissions not exceeding about 40 nm, and preferably not exceeding about 30 nm in width and symmetric about the center, in contrast to the emission bandwidth of about 70-100 nm for a typical dye molecule, with a red tail which may extend the bandwidth out as much as another 100 nm. It should be noted that the bandwidths referred to are determined from measurement of the width of the emissions at half peak height (FWHM), and are appropriate in the range of 200 nm to 2000 nm.

By use of the term "a broad wavelength band," with regard to the electromagnetic radiation absorption of the semiconductor nanocrystal is meant absorption of radiation having a wavelength equal to, or shorter than, the wavelength of the onset radiation (the onset radiation is understood to be the longest wavelength (lowest energy) radiation capable of being absorbed by the semiconductor nanocrystal), which occurs near to, but at slightly higher energy than the "narrow wavelength band" of the emission. This is in contrast to the "narrow absorption band" of dye molecules that occurs near the emission peak on the high-energy side, but drops off rapidly away from that wavelength and is often negligible at wavelengths further than 100 nm from the emission.

The term "detectable signal," as used herein, is meant to include emission by the semiconductor nanocrystal of electromagnetic radiation, including visible or infrared or ultraviolet light and thermal emission; and any other signal or change in signal emanating from the semiconductor nanocrystal evidencing scattering (including diffraction) and/or absorption in response to exposure of the semiconductor nanocrystal to radiation.

By use of the term "detectable substance" is meant an entity or group or class of groups, the presence or absence of which, in a material such as a biological material, is to be ascertained by use of the semiconductor nanocrystal probe of the invention.

The semiconductor nanocrystals useful in the practice of the invention and this example include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. As mentioned above, the use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

Formation of nanometer crystals of Group III-V semiconductors is described in Alivisatos et al. U.S. Pat. No. 5,751,018; Alivisatos et al. U.S. Pat. No. 5,505,928; and Alivisatos et al. U.S. Pat. No. 5,262,357, which also describes the formation of Group II-VI semiconductor nanocrystals, and which is also assigned to the assignee of this invention. Also described therein is the control of the size of the semiconductor nanocrystals during formation using crystal growth terminators. The teachings of Alivisatos et al. U.S. Pat. No. 5,751,018, and Alivisatos et al. U.S. Pat. No. 5,262,357 are each hereby specifically incorporated by reference.

In one embodiment, the nanocrystals are used in a core/shell configuration wherein a first semiconductor nanocrystal forms a core ranging in diameter, for example, from about 20 Å to about 100 Å, with a shell of another semiconductor nanocrystal material grown over the core nanocrystal to a thickness of, for example, 1-10 monolayers in thickness. When, for example, a 1-10 monolayer thick shell of CdS or ZnS is epitaxially grown over a core of CdSe, there is a dramatic increase in the room temperature photoluminescence quantum yield. Formation of such core/shell nanocrystals is described more fully in a publication by one of us with others entitled "Epitaxial Growth of Highly Luminescent CdSe/CdS Core/Shell Nanocrystals with Photostability and Electronic Accessibility," by Peng, Schlamp, Kadavanich, and Alivisatos, published in the Journal of the American Chemical Society, Volume 119, No. 30, 1997, at pages 7019-7029, the subject matter of which is hereby specifically incorporated herein by reference.

The semiconductor nanocrystals used in these examples will have a capability of absorbing radiation over a broad wavelength band. This wavelength band includes the range from gamma radiation to microwave radiation. In addition, these semiconductor nanocrystals will have a capability of emitting radiation within a narrow wavelength band of about 40 nm or less, preferably about 30 nm or less, thus permitting the simultaneous use of a plurality of differently colored semiconductor nanocrystal probes with different semiconductor nanocrystals without overlap (or with a small amount of overlap) in wavelengths of emitted light when exposed to the same energy source. Both the absorption and emission properties of semiconductor nanocrystals may serve as advantages over dye molecules that have narrow wavelength bands of absorption (e.g., about 30-50 nm) and broad wavelength bands of emission (e.g. about 100 nm) and broad tails of emission (e.g., another 100 nm) on the red side of the spectrum. Both of these properties of dyes impair the ability to use a plurality of differently colored dyes when exposed to the same energy source.

Furthermore, the frequency or wavelength of the narrow wavelength band of light emitted from the semiconductor nanocrystal may be further selected according to physical properties, such as size, of the semiconductor nanocrystal. The wavelength band of light emitted by the semiconductor nanocrystal, formed using the above embodiment, may be determined by either (1) the size of the core, or (2) the size of the core and the size of the shell, depending on the composition of the core and shell of the semiconductor nanocrystal. For example, a nanocrystal composed of a 3 nm core of CdSe and a 2 nm thick shell of ZnS will emit a narrow wavelength band of light with a peak intensity wavelength of 560 nm.

A plurality of alternatives to changing the size of the semiconductor nanocrystal in order to selectively manipulate the emission wavelength of semiconductor nanocrystals exists. These alternatives include: (1) varying the composition of the nanocrystal, and (2) adding a plurality of shells around the core of the nanocrystal in the form of concentric shells. It should be noted that different wavelengths can also be obtained in multiple shell type semiconductor nanocrystals by respectively using different semiconductor nanocrystals in different shells, i.e., by not using the same semiconductor nanocrystal in each of the plurality of concentric shells.

Selection of the emission wavelength by varying the composition, or alloy, of the semiconductor nanocrystal is old in the art. As an illustration, when a CdS semiconductor nanocrystal, having an emission wavelength of 400 nm, may be alloyed with a CdSe semiconductor nanocrystal, having an emission wavelength of 530 nm. When a nanocrystal is prepared using an alloy of CdS and CdSe, the wavelength of the emission from a plurality of identically sized nanocrystals may be tuned continuously from 400 nm to 530 nm depending on the ratio of S to Se present in the nanocrystal. The ability to select from different emission wavelengths while maintaining the same size of the semiconductor nanocrystal may be important in applications which require the semiconductor nanocrystals to be uniform in size, or for example, an application which requires all semiconductor nanocrystals to have very small dimensions when used in application with steric restrictions.

This could include matching of redox potential between inorganic NCs (bandgap and surface states) to redox potential of peptide/protein inorganic-organic conjugates for efficient electron transfer between the two. For example: Light activated enzymes.

The bioactivation peptides in these examples were designed to recognize and bind the surface of CdSe/ZnS quantum dot nanoparticles. It is to be understood that the peptide sequence and coatings of this example will also coat and function with particles other than quantum dots. Amino acids with chemical and physical characteristics (hydrophilicity/hydrophobicity, charges and reactivity) allow the binding of the ZnS layer of nanoparticles (of approximately 2-10 nm in size, though it is to be understood that the invention is not limited to nanoparticles of this size.

A non-limiting example of the MRP is Cha-C-C-Cha-C-C-Cha-C-C-Cha (SEQ. ID. NO. 1) with Cha standing for Cyclohexyl alanine and C for cysteine. It is to be understood that the invention does not require alanine to be substituted with a cyclohexyl group; however, cyclohexyl groups are preferred. All synthesis used N-Boc or F-moc protecting groups and sequences may be N-acetylated and/or C-carboxylated. The bioactivation peptides are added directly onto the particles and allowed to form a good dispersion of the quantum dots in DMSO and subsequently yielded stable and highly monodisperse dilutions of the nanocrystals in water and buffer. Stability in water and buffers is enhanced by the addition of a hydrophilic sequence at the N-terminus of the Cha-C-C-Cha . . . sequence. The following sequence was used: G-S-E-S-G-G-S-E-S-G-Cha-C-C-Cha-C-C-Cha-C-C-Cha (SEQ. ID. NO. 2).

In accordance with this example, various sequences of different length are attached on the surface of CdSe/ZnS nanoparticle with the same Cha-C-C-Cha-C-C-Cha-C-C-Cha MRP sequence being present. Table 1 sets forth examples of various bioactivation peptide sequences used to solubilize quantum dots.

TABLE 1

Various Peptide Sequences to Solubilize Quantum Dots

| Name | Sequence |
| --- | --- |
| ChaCha | NH2-Cha-C-C-Cha-C-C-Cha-C-C-Cha-Carboxamide (SEQ. ID. NO. 1) |
| ChaCha acetylated | acetylated-Cha-C-C-Cha-C-C-Cha-C-C-Cha-Carboxamide |
| ChaCha E swimmer | NH2-G-S-E-S-G-G-S-E-S-G-Cha-C-C-Cha-C-C-Cha-C-C-Cha-Carboxamide (SEQ. ID. NO. 2) |
| CH3 | acetylated-G-S-E-S-G-G-S-E-S-G-Cha-C-C-Cha-C-C-Cha-C-C-Cha-Carboxamide (SEQ. ID. NO. 6) |
| COOH | acetylated-G-S-S-S-G-G-S-S-S-G-Cha-C-C-Cha-C-C-Cha-C-C-Cha-Carboxamide (SEQ. ID. NO. 3) |
| NLS | acetylated-G-P-K-K-K-R-K-V-G-G-S-E-S-G-G-S-E-S-G-Cha-C-C-Cha-C-C-Cha-C-C-Cha-Carboxamide (SEQ. ID. NO. 4) |
| K swimmer | acetylated-K-G-S-E-S-G-G-S-E-S-G-Cha-C-C-Cha-C-C-Cha-C-C-Cha-Carboxamide (SEQ. ID. NO. 5) |
| Biotin | Biotin-Cha-C-C-Cha-C-C-Cha-C-C-Cha-Carboxamide |

While not wishing to be bound by any particular theory or principle, it is believed that the binding on surface of the peptide is promoted by the presence of cysteines or other amino acid binding clusters that can be chelated or covalently bound on Zn at the surface of the particle. The spacing between two adjacent cysteines is thought to be similar to that of two Zn (3.82 A). Multiple repeats of cysteine/Zn double bounds probably increases the stability of the peptides on surface. The presence of hydrophobic amino acid spacers in between cysteine clusters also favors the stability of Zn/Cysteine bound by water exclusion and is important for surface ordering (minimizes energy levels at the surface/water interface). The inclusion of hydrophilic amino acids at the N-terminal enhances the solubility of the nanoparticle and provides chemical handles for further chemistry and bioconjugation. This example contemplates that a wide variety of chemical groups can be added on the surface of quantum dots by careful selection of amino acids in accordance with the desired target molecule. In addition, active sequences can be directly dialed in the peptide sequence leading to bio-activated semiconductor nanoparticles. Bioconjugation using linking compounds to attach active molecules to particles can thus be shortcut in some cases.

The unique capability of the bioactivation sequences to bind the surface of CdSe/ZnS nanocrystals was demonstrated by solubilization assays using sequences of ChaCha E swimmer in which the hydrophobic cyclohexyl alanine HS's were replaced by alanine. This substitution led to aggregations of particles during the reaction and thus lack of migration on electrophoresis gels. Similarly replacing the cysteines in the binding clusters with alanine gave unstable particles that flocculate rapidly after solubilization in aqueous solvents. The use of random peptide sequences as the MRP also failed to solubilize nanoparticles.

Peptide sequences from Table 1 were also shown to react directly on CdSe core in addition to the ZnS layer. The quantum dot core can be solubilized directly in water and will maintain a sufficient fluorescent signal to be detected on agarose gels. As expected, the bandwidth of the CdSe in the gel is small since the size distribution of cores is more homogenous than that of core/shell particles. Cores migrate further in the gel since they are smaller than core/shells.

Once soluble in water, quantum dots are usually purified from excess peptides. Purification can be done via dialysis techniques or ultra-filtration on membrane of given molecular weight cut off (MWCO).

The presence of bioactivation peptides on the surface of the quantum dot particles was confirmed by Fournier Transform Infrared studies on purified quantum dots. Particles were dried from water under a nitrogen flow and prepared in KBr pellets. The spectra showed strong absorbance at wave numbers corresponding to typical amide I and amide II bands in the peptide covered quantum dots. These bands were detected for the preparation of peptides alone in the same condition but were lacking for nanocrystals dried from TOPO/butanol.

The optical properties of water-soluble particles are similar to that of the nanocrystals in hydrophobic solvents. Absorption and emission spectra are unaffected by the presence of the bioactivation peptides on the surface.

The physical characterization of soluble semiconductor nanoparticles also shows that the monodispersion of quantum dots is conserved after the addition of bioactivation peptides on the particle surface. Each nanocrystal is solubilized without forming aggregates. Statistics of size distribution by AFM and TEM before and after solubilization in aqueous solvents confirm the absence of aggregates and show that the nanocrystals are unaffected by the surface chemistry.

Since quantum dots covered with bioactivation peptides are monodisperse, biocompatible and soluble in aqueous environment they can be easily analyzed with standard biological techniques such as gel electrophoiesis or High Pressure Liquid Chromatography (HPLC). Nanocrystals, as shown previously, can easily migrate in agarose and polyacrylamide gels. For gel electrophoresis, the migration distance can be correlated to the molecular weight of the nanocrystals (thus to their size) and/or to the charge on the particles. The charge on the particles is influenced by the charge of the bioactivation peptides used. Different size particles covered with the same bioactivation peptides are expected to bear a similar charge. Yet since they have different sizes they should migrate at different position on a gel. This size separation was demonstrated on agarose gels for three colors quantum dots of different sizes (Green: 2.7 nm; Yellow: 5.2 nm and Red: 7.0 nm). Such separations were reproducible at different percentage of agarose gels (3-0.5%), in polyacrylamide gels, for different voltages and using different bioactivation peptides. Size exclusion HPLC experiments confirmed that the separation of nanocrystals was effectively by size and that the effect of the charge during the chromatography on gel did not influence significantly this separation.

As is apparent from the above, a unique bioactivation peptide sequence can be used to solubilize different size particles with clear separation of these particles by size still being possible. Alternatively, it is possible to solubilize one size particle with different kinds of bioactivation peptide sequences (Table 1). As postulated earlier, the charge around a soluble quantum dot is influenced by the charge of the peptides used. It is thus possible to modify the charge of a given size of particles simply by choosing bioactivation peptides of different charges. To verify this property, the same batch of green nanocrystals was solubilized with 4 different peptide sequences of various charges corresponding to the sequences in Table 1 (SEQ. ID. NOS. 4, 3, 6 and 2). The four preparations were purified and then loaded on agarose gels for electrophoresis analysis and on a SEC HPLC column for chromatographic characterization. It was observed that the same size nanocrystals with different charged bioactivation peptides migrate to different positions. Yet, when separated under conditions where no electric field is applied (by size only), all the particles have the same retention time, thus similar molecular weight and similar size.

The use of bioactivation peptides attached to quantum dots not only provides water solubility and chemical handles, but also allows the control of the charge, and possibly other properties such as hydrophobicity, hydrophilicity, polarity, and reactivity. Simply by varying the bioactivation peptides, it is possible to engineer semiconductor nanoparticles and to dial in desired characteristics.

These examples of the invention demonstrate that the use of bioactivation peptides to modify semiconductor nanoparticles offers multiple advantages. Apart from full biocompatibility, this chemistry is extremely versatile and various chemical groups, natural or unnatural, can be introduced by a simple change of amino acids. In addition peptide synthesis chemistry has been widely used and is extremely well characterized. This offers full control of what is on the surface of the quantum dots. Any chemical group present in proteins can be added to the MRP as a functional group and thus on the nanocrystals surface. From the thiol of a cysteine, the N-terminal amine of any amino acids, to more complex histidine tags, or even active sequences (NLS, peptidase responsive sequences . . . ) may be added to the MRP. Simple chemical groups ($NH_2$, COOH, SH, OH . . . ) can be used for further bioconjugation using conventional reagents and protocols.

Figure 4:
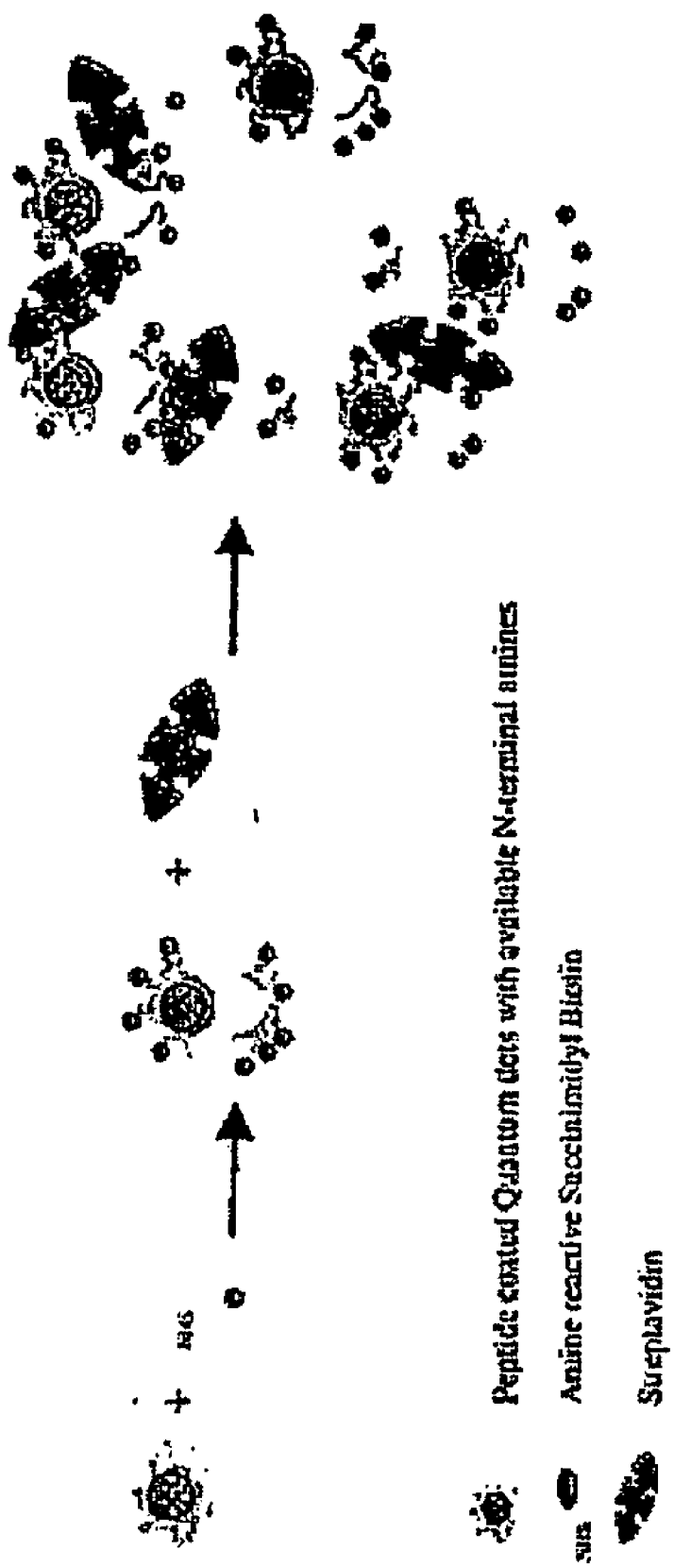
FIG. 4 is a pictorial representation of the treatment of a particle with bioactivation peptides to attach a biotin conjugation agent to the particle.

The attachment of a biotin moiety on the surface of CdSe/ZnS semiconductors is shown diagrammatically in FIG. 4 using succinimidyl chemistry with the reaction of a NHS-biotin on the N-termial amine of a peptide sequence on the surface of particles. The presence of biotin on the particle surface is detected by a simple gel retardation assay in the presence of Streptavidin.

As mentioned previously, the nanoparticles can be directly encoded in one step if the peptide sequences used for solubilization contain an active element This element can be a biotin (Table 1), or a targeting peptide sequence. This invention contemplates that bioconjugation steps can be skipped by bio-activating quantum dots with motif peptides that are included in the peptide sequence to be attached to the CdSe/ZnS nanocrystrals surfaces.

The use of bioactivation peptides to provide biological functions to quantum dots offers an easy, reproducible, versatile and reliable chemistry. It yields biocompatible particles on which any known bioconjugation scheme can be applied. The invention is unique in the sense that it is a one step chemical reaction requiring no spacer, pretreatment or preparation of the nanocrystal surfaces with linkers or other surface modulation grids. The binding is highly specific, probably covalent, by chelation, cysteine or other binding cluster on the surface of the peptide to ions on the surface of the nanoparticle. The invention uses the unique properties of amino acids to make a stable interface with inorganic or organic materials present on the particle surface. This invention, as described herein, allows the binding of any peptide surface or proteins (when presenting the required sequence) to photon emitting particles and other semiconductors, magnetic, radioactive, dielectric and metal particles.

The present invention is useful in various fields including peptide library screening/Phage display; in vivo/in vitro drug screening and mass screening (using encoded quantum dots able to respond to drug stimulus by targeting a specific part, of a cell); in vivo/in vitro multicolor assays (all quantum dots application in fluorescence microscopy (Confocal), fluorescence in-situ hybridization (FISH), fluorescence correlation spectroscopy (FCS), flow cytometry, beads encoding); transmission electron microscopy (cell staining for enhanced contrast of sub cellular compartments for transmission electron microscopy (TEM)), cryogenic electron microscopy (CryoEM); atomic force microscopy (AFM) (use as probes/standards in AFM/confocal combinations; Assays based on peptide/peptide interaction (scratch peptide technology), histidin (HIS) tag, protein/peptide interaction (nuclear localization signal/sequence (NLS)) signal sequence, protease responsive sequence, phosphatase responsive sequence . . . ), peptide/DNA interaction (DNA groove, Zn fingers, leucine Zippers . . . ), and peptide/RNA interaction; molecular dynamic of Ab/Ag interactions by single molecule detection/quenching or single molecule fluorescence resonance energy transfer (FRET); molecular rules (FRET, co-localization), molecular compass (rods+Qdots); crystallography 2D, 3D arrays for protein structure analysis, or photoluminescence devices; solid phase hybridization assay using quantum dots as a support (DNA directly on Qdots, efficiency determined by quenching or fluorescence enhancement) polymerase chain reaction (PCR); enzyme kinetics assays; bar code system by assembly of various amounts and various types of quantum dots (peptide Velcro technology or antisense peptides); therapy using semiconductor properties (mitochondria electron flux disruption, neurological application with electron jumping); photo-activation of enzyme using conducting peptides (cytochrome C); use of complex nanostructures for biocompatible devices, or for their catalytic properties; peptide-nucleic acid (PNA) technology.

Figure 3:
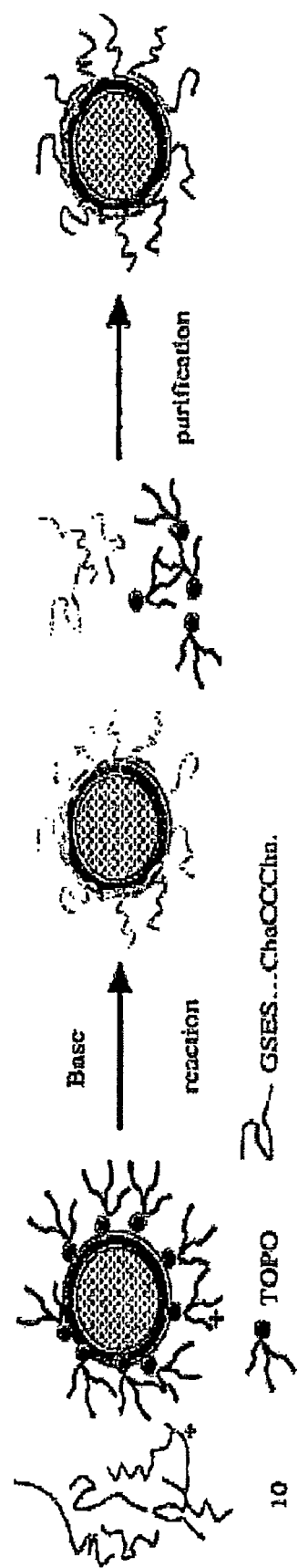
FIG. 3 is a pictorial representation of the treatment of a particle with bioactivation peptides to increase the solubility of the particle.

The following is a non-limiting example of solubilization (bioactivation) of CdSe/ZnS quantum dots as depicted in FIG. 3:

25 µl of TOPO coated quantum dots were taken from the mother solution in butaniol (Mother solution consisted of 40 mg CdSe core reacted with ZnS in a final volume of Butanol+TOPO of about 8 ml).

the QD's were precipitated with 25 µl methanol and centrifuged in a glass vial the residual methanol was discarded the paste was re-dissolved with 650 ul of pyridine (anhydrous)

4.0 mg (this amount is not fixed, but variable and is easily determined by the amount of QD's in pyridine) of crude peptide (any one of the bioactivation peptides identified in Table 1) was weighed and dissolved in DMSO (50 µl) and mixed with the QD's in pyridine this mixture was vortexed for 10 seconds next was added 14 µl of Trimethyl ammonium hydroxide (25% in Methanol)

this mixture was vortexed quickly for 20 seconds centrifuged then the residual pyridine was discarded next 500 µl of methyl sulfoxide (DMSO) was added on the precipitate the precipitate was then re-dissolved and then diluted in water/buffer for exchange DMSO against water/buffer on a G-25 sephadex column An example of the preparation of bioactivated nanoparticles having two different bioactivation peptides attached to the particle surfaces is shown pictorially in FIG. 5 and described as follows:

25 to 30 µl of TOPO coated quantum dots (QD's) were taken from the mother solution in TOPO/butanol.

Precipitated with methanol (anhydrous) and centrifuge in a glass vial.

The residual methanol was discarded.

The paste was re-dissolved with pyridine (anhydrous) to an Optical Density at the first exciton peak of 0.25.

2.0 mg of crude biotinylated peptides biotin-hydrophilic peptide-MRP carboxamide) and 2.0 mg of pegylated peptides peg-MRP carboxamide) were weighed, mixed and dissolved in 50 µl Methyl Sulfoxide (DMSO) and mixed with 450 µl of QD's in pyridine.

The mixture was vortexed for 5 seconds.

Then 12 µl of Trimethyl ammonium hydroxyde (25% (w/v) in Methanol) is added.

Mixture was mixed quickly for 5 seconds.

Centrifuged.

The residual pyridine (supernatant) was discarded.

The paste of bioactivated nanocrystalline particles obtained was then dissolved with 500 µl of DMSO The precipitate was allowed to slowly re-dissolve in DMSO and then was diluted in water/buffer or exchanged against water/buffer on a G-25 sephadex column.

The bioactivated nanocrystalline particles in water/buffer were dialyzed to purify the samples from unbound excess peptides.

As set forth in the preceding example, modulation of the NCs properties using different peptides can be achieved. We initially solubilized NCs with a biotinylated peptide (Biotin—Table 1) and tested this biotin-NC substrate for activity in a gel shift experiment with streptavidin (see FIG. 4). This substrate appears to be efficiently recognized by both streptavidin and avidin. This shows that NCs can directly be bioactivated without a need for bioconjugation. While bioconjugation usually requires some post-reaction purifications and analysis of the conjugation efficiency, the use of directly active peptides in accordance with the present invention significantly simplifies the production of bioactive NCs. No further processing of the samples is required after peptide coating. Yet, we also confirmed that conjugation of bio-molecules to the NCs was possible using conventional linkers. We used a succinimidyl ester derivatized biotin to attach a biotin moiety on the terminal amine or on the lysine residue of NCs coated with a bioactivation peptide. Similar results to that of biotinylated peptides directly reacted on the NCs were obtained by gel shift assays.

Although the biotinylated bioactivation peptide coated NCs were able to react well with streptavidin targets in solution, they were less efficient when tested against immobilized avidin and streptavidin proteins (e.g., 96 wells plate format, streptavidin on actin filaments). We assumed that this lack of activity in "solid phase" was related to steric hindrance problems of the active peptides on the NCs surface. This hindrance may limit the freedom of interaction of the biotin with its target. To overcome this problem we mixed different amounts of bioactivation peptides: one targeting peptide, biotin-hydrophilic peptide-MRP carboxamide, and a shorter peptide with a solubility agent peg-MRP carboxamide on the surface of the NCs. This ratiometric approach allows one to improve the molecular interaction of NCs with their target. The non-active shorter peptide sequence was chosen not only to reduce the steric hindrance but also to improve the solubility of the NCs. Short pegylated bioactivation peptides containing the surface recognition part and one or more polyethylene glycol groups could efficiently solubilize the NCs, improve the reactivity of other bioreactive peptides and also allowed decreases of non specific binding without affecting the colloidal and photophysical properties of the particles.

This new approach for the surface chemistry allowed us to perform the first targeting of bioactivation peptide coated NCs in living cells. NCs-biotin-peg conjugates (biotin-hydrophilic peptide-MRP-carboxamide plus peg-MRP-carboxamide) were reacted on living HeLa cells over-expressing CD14 receptors fused with an avidin. The CD14 receptors are part of the glycosyl-phophatidyl-inositol (GPI) anchored proteins family. This chimeric CD14-avidin protein is thus very useful to study the dynamics of lipid-anchored receptors in the cytoplasmic membrane of living cells as well as their recycling. The use of bioactivated NCs, in this context, offer the unique advantages of allowing long-term and real-time studies of these processes with single molecule sensitivity. We found that NCs-biotin-peg conjugates can specifically recognize the over-expressed CD14-Av fusion proteins. Movies of the recycling processes of CD14 receptors in living HeLa cells could easily be produced taking advantage of the high photostability of the NCs probes. This type of bioactivated NC probe in accordance with the present invention allows one to analyze the diffusion times and diffusion patterns of single CD14-Av-biotin-peg-NCs as well CD14-Av-biotin-peg-NCs endocytic vesicles in different part of living HeLa cells (membrane, endosome, golgi) in order to shine light on the molecular behavior of CD14 receptors. These results may allow a better understanding of the molecular dynamics of glycosyl-phophatidyl-inositol (GPI) anchored proteins.

Although the foregoing invention has been described in some detail for purposes of clarity of understanding, those skilled in the art will appreciate that various adaptations and modifications of the just described preferred embodiments can be configured without departing from the scope and spirit of the invention. The described embodiments should be taken as illustrative and not restrictive, and the invention should not be limited to the details given herein but should be defined by the following claims and their full scope of equivalents.

---

What is claimed is:

1. A bioactivated particle, comprising:
   a quantum dot that includes a surface; and
   at least one bioactivation peptide attached to said surface of said quantum dot, said bioactivation peptide comprising a molecular recognition part that is bound to the surface of said quantum dot and one or more functional parts, said molecular recognition part comprising an amino-end and a carboxy-end and comprising one or more hydrophobic spacers and one or more binding clusters and wherein said functional part(s) is attached to said molecular recognition part at said amino-end and/or said carboxy-end,
   wherein said binding cluster is directly bound to said surface of said quantum dot and comprises an amino acid independently selected from the group consisting of cysteine, methionine, and histidine,
   wherein said hydrophobic spacer comprises an amino acid modified to be hydrophobic independently selected from the group consisting of cyclohexyl-substituted alanine, cyclohexyl-substituted glycine, cyclohexyl-substituted isoleucine, cyclohexyl-substituted leucine, cyclohexyl-substituted methionine, cyclohexyl-substituted arginine, cyclohexyl-substituted valine, and cyclohexyl-substituted tryptophan,
   wherein said bioactivation peptide comprises the sequence Cha-C-C-Cha-C-C-Cha-C-C-Cha [SEQ. ID. NO. 1], and
   wherein Cha is cyclohexyl alanine and C is cysteine.

2. A bioactivated particle according to claim 1 where said binding cluster consists essentially of two cysteines.

3. A bioactivated particle according to claim 1 wherein said hydrophobic amino acid is cyclohexyl alanine.

4. A bioactivated particle according to claim 2 wherein said hydrophobic spacer is cyclohexyl alanine.

5. A bioactivated particle according to claim 1 wherein said molecular recognition part comprises at least three binding clusters which are located alternately between at least four hydrophobic spacers.

6. A bioactivated particle according to claim 5 wherein said binding cluster consists essentially of two cysteines and said hydrophobic spacer consists essentially of cyclohexyl alanine.

7. A bioactivated particle according to claim 1 wherein said quantum dot comprises inorganic material at said surface.

8. A bioactivated particle according to claim 1 wherein the diameter of said quantum dot is between 0.1 and 100 nanometers.

9. A bioactivated particle according to claim 7 wherein said inorganic material is selected from the group consisting of semiconductors comprising elements from column(s) II and VI, III and V, and/or IV of the periodic table, metallic materials, magnetic materials and dielectric materials.

10. A bioactivated particle according to claim 9 wherein the diameter of said quantum dot is between 0.1 and 100 nanometers.

11. A bioactivated particle according to claim 1 wherein said functional part(s) comprise one or more functional agent(s) selected from the group consisting of solubility agents, conjugation agents, targeting agents, therapeutic agents, imaging agents, detection agents, recognition, agents and diagnostic agents.

12. A bioactivated particle according to claim 1 wherein said functional part(s) consist essentially of one or more solubility agent(s).

13. A bioactivated particle according to claim 1 wherein said functional part(s) comprise a solubility agent attached to said molecular recognition part and one or more functional agent(s) attached to said one or more solubility agents) wherein said functional agent(s) is selected from the group consisting of conjugation agents, targeting agents, therapeutic agents, imaging agents, detection agents, recognition agents and diagnostic agents.

14. A bioactivated particle according to claim 12 wherein said solubility agent is selected from the group consisting of hydrophilic peptides, polyethylene glycol, poly(ethylene oxide), polyelectrolytes and sugars.

15. A bioactivated particle according to claim 14,
    wherein a first portion and second portion of said at least one bioactivation peptide, are attached to said particle surface and
    wherein said first portion comprises functional part(s) that are different from the functional part(s) of said second portion.

16. A bioactivated particle according to claim 15,
    wherein said first portion of said at least one bioactivation peptide includes a functional part that comprises a first solubility agent that consists of a hydrophilic peptide and
    wherein said second portion of said at least one bioactivation peptide includes a functional part that comprises a second solubility agent that consists of polyethylene glycol.

17. A bioactivation peptide for use in treating quantum dots having a surface to form bioactivated particles, said bioactivation peptide comprising:
    a molecular recognition part that is bindable to said surface of said quantum clot and one or more functional parts, said molecular recognition part including an amino-end and a carboxy-end and comprising one or more hydrophobic spacers and one or more binding clusters and wherein said functional part(s) is attached to said molecular recognition part at said amino-end and/or said carboxy-end,
    wherein said binding cluster is directly bindable to said surface of said quantum dot and comprises an amino acid independently selected from the group consisting of cysteine, methionine, and histidine and
    wherein said hydrophobic spacer comprises an amino acid modified to be hydrophobic independently selected from the group consisting of cyclohexyl-substituted alanine, cyclohexyl-substituted glycine, cyclohexyl-substituted isoleucine, cyclohexyl-substituted leucine, cyclohexyl-substituted methionine, cyclohexyl-substituted arginine, cyclohexyl-substituted valine, and cyclohexyl-substituted tryptophan,
    wherein the molecular recognition part comprises the sequence Cha-C-C-Cha-C-C-Cha-C-C-Cha [SEQ. ID. NO. 1], and
    wherein Cha is cyclohexyl alanine and C is cysteine.

18. A bioactivation peptide according to claim 17, wherein said binding cluster consists essentially of two cysteines.

19. A bioactivation peptide according to claim 17, wherein said hydrophobic amino acid is cyclohexyl alanine.

20. A bioactivation peptide according to claim 18 wherein said hydrophobic spacer is cyclohexyl alanine.

21. A bioactivation peptide according to claim 17 wherein said molecular recognition part comprises at least three binding clusters which are alternately located between at least four hydrophobic spacers.

22. A bioactivation peptide according to claim 21 wherein said binding clusters each consists essentially of two cysteines and said hydrophobic spacers each consists essentially of cyclohexyl alanine.

23. A bioactivation peptide according to claim 17 wherein said quantum dot to which said molecular recognition part is bindable comprises inorganic material at said surface.

24. A bioactivation peptide according to claim 23 wherein the diameter of said particle is between 0.1 and 100 nanometers.

25. A bioactivation peptide according to claim 17 wherein said functional part(s) comprises one or more functional agent(s) selected from the group consisting of solubility agents, conjugation agents, targeting agents, therapeutic agents, imaging agents, detection agents, recognition agents and diagnostic agents.

26. A bioactivation peptide according to claim 17 wherein said functional part(s) consist essentially of one or more solubility agent(s).

27. A bioactivation peptide according to claim 17 wherein said functional part(s) comprise one or more solubility agents attached to said molecular recognition part and one or more functional agent(s) attached to said one or more solubility agent(s) wherein said functional agents) is selected from the group consisting of conjugation agents, targeting agents, therapeutic agents, imaging agents, detection agents, recognition agents and diagnostic agents.

28. A bioactivation peptide according to claim 26 wherein said solubility agent is selected from the group consisting of hydrophilic peptides, polyethylene glycol, polyethylene oxide), polyelectrolytes and sugars.

29. A composition of matter comprising bioactivated particles according to claim 1 suspended in an aqueous medium.

30. A composition of matter comprising bioactivated particles according to claim 12 suspended in an aqueous medium.

31. A composition of matter comprising bioactivated particles according to claim 13 suspended in an aqueous medium.

32. A composition of matter comprising bioactivated particles according to claim 15 suspended in an aqueous medium.

33. A composition of matter comprising bioactivated particles according to claim 16 suspended in an aqueous medium.

34. A method for making a bioactivated particle that is soluble in an aqueous medium, said method comprising the steps of:
provZiding a quantum dot that includes a surface; and
treating the surface of said quantum dot with a sufficient amount of a bioactivation peptide according to claim 17 to make said bioactivated particle soluble in said aqueous medium.

35. A method for making a bioactivated particle that is soluble in an aqueous medium, said method comprising the steps of:
providing a quantum dot that includes a surface; and
treating the surface of said quantum dot with a sufficient amount of a bioactivation peptide according to claim 26 to make said bioactivated particle soluble in said aqueous medium.

36. A method for making a bioactivated particle that is soluble in an aqueous medium, said method comprising the steps of:
providing a quantum dot that includes a surface; and
treating the surface of said quantum dot with a sufficient amount of a bioactivation peptide according to claim 27 to make said bioactivated particle soluble in said aqueous medium.

37. A bioactivated particle having the formula $$[FP_1]-[HS]-\{[BC]-[HS]\}_m,$$
$$\phantom{[FP_1]-[HS]-\{[BC]}|$$
$$\phantom{[FP_1]-[HS]-\{[BC]}[QD]$$

$$[HS]-\{[BC]-[HS]\}_m-[FP_2], \quad \text{or}$$
$$\phantom{[HS]-\{[BC]}|$$
$$\phantom{[HS]-\{[BC]}[QD]$$

$$[FP_1]-[HS]-\{[BC]-[HS]\}_m-[FP_2],$$
$$\phantom{[FP_1]-[HS]-\{[BC]}|$$
$$\phantom{[FP_1]-[HS]-\{[BC]}[QD]$$

wherein [QD] is a quantum dot,
wherein [BC] is a binding cluster comprising an amino acid independently selected from the group consisting of cysteine, methionine, histidine, and combinations,
wherein [HS] is a hydrophobic spacer comprising an amino acid modified to be hydrophobic independently selected from the group consisting of cyclohexyl-substituted alanine, cyclohexyl-substituted glycine, cyclohexyl-substituted isoleucine, cyclohexyl-substituted leucine, cyclohexyl-substituted methionine, cyclohexyl-substituted arginine, c cyclohexyl-substituted valine, and cyclohexyl-substituted tryptophan,
wherein m is at least 1,
wherein [FP$_1$] and [FP$_2$] may be the same or different and are functional parts selected from the group consisting of a solubility agent, conjugation agent, targeting agent, therapeutic agent, imaging agent, detection agent, recognition agent, and diagnostic agent,
wherein the sequence $\{[BC]\text{-}[HS]\}_m$ comprises the sequence Cha-C-C-Cha-C-C-Cha-C-C-Cha [SEQ. ID. NO. 1], and
wherein Cha is cyclohexyl alanine and C is cysteine.

38. The bioactivated particle of claim 37,
wherein [BC] is a binding cluster consisting of at least one cysteine.
wherein [HS] is a hydrophobic spacer consisting of at least one cyclohexyl alanine,
wherein m is at most 3, and
wherein [FP$_1$] and [FP$_2$] may be the same or different and are functional parts selected from the group consisting of a hydrophilic peptide, polyethylene glycol, poly(ethylene oxide), a polyelectrolyte, polyethylene imine, a sugar, cellobiose, sucrose, sialic acid, and combinations.

39. A bioactivation peptide having the formula:

$$[FP_1]\text{-}[MRP], [MRP]\text{-}[FP_2], \text{ or } [FP_1]\text{-}[MRP]\text{-}[FP_2],$$

wherein [FP$_1$] and [FP$_2$] may be the same or different and are functional parts selected from the group consisting of amide, acetyl, carboxamide, carboxyl, polyethylene glycol (PEG), NHS ester, keto, thiol, 1,4,7,10-tetraazacyclododecane-1,4,7,10-tetraacetic acid (DOTA), Ni-NTA, I, Yt, tritium, a metallo texaphyrin, taxol, herceptin, fluorescein, bromothymol blue, a hydrophilic peptide, biotin, avidin, streptavidin, lysine, cysteine, aspartic acid, DNA, transferrin, an antibody, a single chain fragment, G-S-E-S-G-G-S-E-S-G [SEQ. ID. NO. 6], G-S-S-S-G-G-S-S-S-G [SEQ. ID. NO. 7], G-P-K-K-K-R-K-V-G-G-S-E-S-G-G-S-E-S-G [SEQ.ID.NO. 8], K-G-S-E-S-G-G-S-E-S-G [SEQ. ID. NO. 9], and combinations,
wherein [MRP] is a molecular recognition part consisting of Cha-C-C-Cha-C-C-Cha-C-C-Cha [SEQ. ID. NO. 1], and wherein Cha is cyclohexyl alanine, C is cysteine, G is glycine, S is serine, E is glutamic acid, P is proline, K is lysine, R is arginine, and V is valine.

40. The bioactivation peptide of claim 39, having the formula

[MRP]-[FP$_2$]

wherein [FP$_2$] is selected from the group consisting of PEG, PEG-biotin, hydrophilic peptide-transferrin, and hydrophilic peptide-tyrosine-DOTA-iodine.

41. The bioactivation peptide of claim 39, selected from the group consisting of NH$_2$-Cha-C-C-Cha-C-C-Cha-C-C-Cha-carboxamide [SEQ. ID. NO. 1], acetylated-Cha-C-C-Cha-C-C-Cha-C-C-Cha-carboxamide [SEQ. ID. NO. 1], NH$_2$-G-S-E-S-G-G-S-E-S-G-Cha-C-C-Cha-C-C-Cha-C-C-Cha-carboxamide [SEQ. ID. NO. 2], acetylated-G-S-E-S-G-G-S-E-S-G-Cha-C-C-Cha-C-C-Cha-C-C-Cha-carboxamide [SEQ. ID. NO. 10], acetylated-G-S-S-S-G-G-S-S-S-G-Cha-C-C-Cha-C-C-Cha-C-C-Cha-carboxamide [SEQ. ID. NO. 3], acetylated-G-P-K-K-K-R-K-V-G-G-S-E-S-G-G-S-E-S-G-Cha-C-C-Cha-C-C-Cha-C-C-Cha-carboxamide [SEQ. ID. NO. 4], acetylated-K-G-S-E-S-G-G-S-E-S-G-Cha-C-C-Cha-C-C-Cha-C-C-Cha-carboxamide [SEQ. ID. NO. 5], and biotin-Cha-C-C-Cha-C-C-Cha-C-C-Cha-carboxamide [SEQ. ID. NO. 1].

42. The bioactivated particle according to claim 1, wherein the at least one bioactivation peptide is selected from the group consisting of NH$_2$-Cha-C-C-Cha-C-C-Cha-C-C-Cha-carboxamide [SEQ. ID. NO. 1], acetylated-Cha-C-C-Cha-C-C-Cha-C-C-Cha-carboxamide [SEQ. ID. NO. 1], NH$_2$-G-S-E-S-G-G-S-E-S-G-Cha-C-C-Cha-C-C-Cha-C-C-Cha-carboxamide [SEQ. ID. NO. 2], acetylated-G-S-E-S-G-G-S-E-S-G-Cha-C-C-Cha-C-C-Cha-C-C-Cha-carboxamide [SEQ. ID. NO. 10], acetylated-G-S-S-S-G-G-S-S-S-G-Cha-C-C-Cha-C-C-Cha-C-C-Cha-carboxamide [SEQ. ID. NO. 3], acetylated-G-P-K-K-K-R-K-V-G-G-S-E-S-G-G-S-E-S-G-Cha-C-C-Cha-C-C-Cha-C-C-Cha-carboxamide [SEQ. ID. NO. 4], acetylated-K-G-S-E-S-G-G-S-E-S-G-Cha-C-C-Cha-C-C-Cha-C-C-Cha-carboxamide [SEQ. ID. NO. 5], and biotin-Cha-C-C-Cha-C-C-Cha-C-C-Cha-carboxamide [SEQ. ID. NO. 1], wherein G is glycine, S is serine, E is glutamic acid, P is proline, K is lysine, R is arginine, and V is valine.

43. The bioactivation peptide according to claim 17, selected from the group consisting of NH$_2$-Cha-C-C-Cha-C-C-Cha-C-C-Cha-carboxamide [SEQ. ID. NO. 1], acetylated-Cha-C-C-Cha-C-C-Cha-C-C-Cha-carboxamide [SEQ. ID. NO. 1], NH$_2$-G-S-E-S-G-G-S-E-S-G-Cha-C-C-Cha-C-C-Cha-C-C-Cha-carboxamide [SEQ. ID. NO. 2], acetylated-G-S-E-S-G-G-S-E-S-G-Cha-C-C-Cha-C-C-Cha-C-C-Cha-carboxamide [SEQ. ID. NO. 10], acetylated-G-S-S-S-G-G-S-S-S-G-Cha-C-C-Cha-C-C-Cha-C-C-Cha-carboxamide [SEQ. ID. NO. 3], acetylated-G-P-K-K-K-R-K-V-G-G-S-E-S-G-G-S-E-S-G-Cha-C-C-Cha-C-C-Cha-C-C-Cha-carboxamide [SEQ. ID. NO. 4], acetylated-K-G-S-E-S-G-G-S-E-S-G-Cha-C-C-Cha-C-C-Cha-C-C-Cha-carboxamide [SEQ. ID. NO. 5], and biotin-Cha-C-C-Cha-C-C-Cha-C-C-Cha-carboxamide [SEQ. ID. NO. 1], wherein G is glycine, S is serine, E is glutamic acid, P is proline, K is lysine, R is arginine, and V is valine.

* * * * *

UNITED STATES PATENT AND TRADEMARK OFFICE
CERTIFICATE OF CORRECTION

| | |
|---|---|
| PATENT NO. | : 7,998,923 B2 |
| APPLICATION NO. | : 10/513567 |
| DATED | : August 16, 2011 |
| INVENTOR(S) | : Pinaud et al. |

It is certified that error appears in the above-identified patent and that said Letters Patent is hereby corrected as shown below:

Column 1, cancel the text in lines 10 – 14 and replace with the following:

-- This invention was made with Government support under Grant No. EB000312 awarded by the National Institutes of Health. The Government has certain rights in this invention. --

Signed and Sealed this
Seventh Day of February, 2012

David J. Kappos
*Director of the United States Patent and Trademark Office*